(12) United States Patent
Kang et al.

(10) Patent No.: US 10,076,309 B2
(45) Date of Patent: Sep. 18, 2018

(54) ULTRASONIC IMAGING APPARATUS AND CONTROL METHOD THEREOF

(71) Applicant: SAMSUNG ELECTRONICS CO., LTD., Suwon-si (KR)

(72) Inventors: Joo Young Kang, Yongin-si (KR); Sung Chan Park, Suwon-si (KR); Jung Ho Kim, Yongin-si (KR); Jong Keun Song, Yongin-si (KR); Su Hyun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 938 days.

(21) Appl. No.: 14/328,096

(22) Filed: Jul. 10, 2014

(65) Prior Publication Data

US 2015/0025383 A1    Jan. 22, 2015

(30) Foreign Application Priority Data

Jul. 19, 2013  (KR) .................. 10-2013-0085219

(51) Int. Cl.
*A61B 8/00* (2006.01)
*A61B 8/08* (2006.01)
(Continued)

(52) U.S. Cl.
CPC .......... *A61B 8/5207* (2013.01); *A61B 5/7235* (2013.01); *G01S 7/5205* (2013.01);
(Continued)

(58) Field of Classification Search
None
See application file for complete search history.

(56) References Cited

U.S. PATENT DOCUMENTS

2002/0049379 A1    4/2002   Adam et al.
2004/0054281 A1*   3/2004   Adam .............. A61B 8/587
                                                600/437
(Continued)

FOREIGN PATENT DOCUMENTS

EP           2690462 A2      1/2014
KR        10-0764414 B1     10/2007
KR     10-2012-0125704 A    11/2012

OTHER PUBLICATIONS

Communication dated Dec. 11, 2014, by the European Patent Office in related application No. 14177719.3-1812.
(Continued)

*Primary Examiner* — Joel F Brutus
(74) *Attorney, Agent, or Firm* — Sughrue Mion, PLLC

(57) ABSTRACT

Disclosed herein are an ultrasonic imaging apparatus which is capable of accurately and quickly estimating a Point Spread Function (PSF) is usable for restoring ultrasonic images, and a control method which is executable by the ultrasonic imaging apparatus. The ultrasonic imaging apparatus includes: a probe; a receive beamformer configured to beamform an ultrasonic signal and to output the beamformed ultrasonic signal; a Point Spread Function (PSF) database configured to store a PSF which is acquired based on a situational variable, and a phase parameter which is determined based on the situational variable, for the beamformed ultrasonic signal; and an image generator configured to select the PSF and the phase parameter from the PSF database based on the beamformed ultrasonic signal, and to perform deconvolution using an estimated PSF based on the selected PSF and the selected phase parameter in order to generate an image.

26 Claims, 16 Drawing Sheets
(6 of 16 Drawing Sheet(s) Filed in Color)

(51) Int. Cl.
  *A61B 5/00* (2006.01)
  *G01S 15/89* (2006.01)
  *G01S 7/52* (2006.01)
(52) U.S. Cl.
  CPC .............. *G01S 15/8977* (2013.01); *A61B 8/56* (2013.01); *A61B 8/565* (2013.01)

(56) References Cited

U.S. PATENT DOCUMENTS

| | | | |
|---|---|---|---|
| 2005/0057392 A1 | 3/2005 | Blunt et al. | |
| 2005/0265621 A1 | 12/2005 | Biggs et al. | |
| 2006/0052703 A1 | 3/2006 | Kumazawa | |
| 2012/0076435 A1* | 3/2012 | Sharma | G06T 1/0064 382/277 |
| 2013/0090559 A1* | 4/2013 | Park | A61B 8/5207 600/443 |

OTHER PUBLICATIONS

Ho-Chul Shin et al; "Estimation of Average Speed of Sound Using Deconvolution of Medical Ultrasound Data"; Ultrasound in Medicine and Biology; vol. 36 No. 4; Apr. 1, 2010; pp. 623-636.

Jooyoung Kang et al; "Fast Non-Blind De-convolution based on 2D Point Spread Function database for real-time ultrasound imaging"; SPIE-IS&T; vol. 8656; Feb. 19, 2013; 6 pages total.

Jooyoung Kang et al; "Parametric Phase Information based 2D Cepstrum PSF Estimation Method for Blind De-convolution of Ultrasound Imaging"; Proceedings of SPIE International Society for Optical Engineering; vol. 9029; Feb. 17, 2014; 6 pages total.

Communication dated Sep. 2, 2016 issued by the European Patent Office in counterpart European Patent Application No. 14177719.3.

Sungchan Park et al., "Minimum variance image blending for robust ultrasound image Deconvolution", Medical Imaging 2014: Ultrasonic Imaging and Tomography, Proc. of SPIE vol. 9040, 90400E, (2014) (pp. 90400E-1-90400E-7, 7 pages Total) doi: 10.1117/12.2043905.

Decision to refuse a European Patent Application dated Dec. 14, 2017, issued by the European Patent Office in counterpart European Patent Application No. 14177719.3.

Oral Proceedings in accordance with Rule 124(4) dated Dec. 14, 2017, issued by the European Patent Office in counterpart European Patent Application No. 14177719.3.

Communication dated May 24, 2017 issued by the European Patent Office in counterpart European Patent Application No. 14177719.3.

* cited by examiner

ULTRASONIC IMAGING APPARATUS AND CONTROL METHOD THEREOF

CROSS-REFERENCE TO RELATED APPLICATION

This application claims priority from Korean Patent Application No. 10-2013-0085219, filed on Jul. 19, 2013 in the Korean Intellectual Property Office, the disclosure of which is incorporated herein by reference in its entirety.

BACKGROUND

1. Field

Exemplary embodiments relate to an ultrasonic imaging apparatus and a control method thereof, and more particularly, to an ultrasonic imaging apparatus which is capable of accurately and quickly estimating a Point Spread Function (PSF) which is usable for restoring ultrasonic images, and a control method which is executable by the ultrasonic imaging apparatus.

2. Description of the Related Art

Medical imaging apparatuses include an X-ray imaging apparatus, a fluoroscopy system, a Computerized Tomography (CT) scanner, a Magnetic Resonance Image (MRI) apparatus, a Positron Emission Tomography (PET) apparatus, and an ultrasonic imaging apparatus.

The ultrasonic imaging apparatus irradiates ultrasonic waves toward the inside of an object, and receives ultrasonic echoes which are reflected from the inside of the object so as to non-invasively acquire section images of the inner tissues of the object or images of blood vessels of the object based on the received ultrasonic echoes.

The ultrasonic imaging apparatus has advantages, including that it is a compact, low-priced apparatus compared to other medical imaging apparatuses, and that it can display images in real time. Also, the ultrasonic imaging apparatus has high safety, since there is no risk for patients to be exposed to radiation such as X-rays. As a result of these advantages, the ultrasonic imaging apparatus is widely used to diagnose conditions relating to the heart, breasts, abdomen, urinary organs, uterus, and other body parts.

SUMMARY

Therefore, it is an aspect of the one or more exemplary embodiments to provide an ultrasonic imaging apparatus which is capable of accurately and quickly estimating a Point Spread Function (PSF) which is usable for restoring ultrasonic images, and a control method which is executable by the ultrasonic imaging apparatus.

Additional aspects of the exemplary embodiments will be set forth in part in the description which follows and, in part, will be obvious from the description, or may be learned by practice of the exemplary embodiments.

In accordance with one aspect of one or more exemplary embodiments, an ultrasonic imaging apparatus includes: a probe configured to irradiate ultrasonic waves toward a target area of an object, to receive at least one ultrasonic echo which is reflected from the target area, to convert the received at least one ultrasonic echo into an electrical signal, and to output the electrical signal as an ultrasonic signal; a receive beamformer configured to beamform the ultrasonic signal and to output the beamformed ultrasonic signal; a Point Spread Function (PSF) database configured to store a PSF which is acquired based on a situational variable, and a phase parameter which is determined based on the situational variable, for the beamformed ultrasonic signal; and an image generator configured to select the acquired PSF and the determined phase parameter from the PSF database based on the beamformed ultrasonic signal, and to perform a deconvolution using a PSF estimated based on the selected PSF and the selected phase parameter in order to generate an image.

In accordance with another aspect of one or more exemplary embodiments, a control method which is executable by an ultrasonic imaging apparatus includes: generating a Point Spread Function (PSF) database which stores a PSF which is acquired based on a situational variable and a phase parameter which is determined based on the situational variable; irradiating ultrasonic waves toward a target area of an object, receiving at least one ultrasonic echo which is reflected from the target area, converting the received at least one ultrasonic echo into an electrical signal, and outputting the electrical signal as an ultrasonic signal; beamforming the ultrasonic signal, and outputting the beamformed ultrasonic signal; and selecting the acquired PSF and the determined phase parameter from the PSF database based on the beamformed ultrasonic signal, and performing a deconvolution using a PSF which is estimated based on the selected PSF and the selected phase parameter in order to generate an image.

In accordance with another aspect of one or more exemplary embodiments, an ultrasonic imaging apparatus includes: a probe configured to irradiate ultrasonic waves toward a target area of an object, to receive at least one ultrasonic echo which is reflected from the target area, to convert the received at least one ultrasonic echo into an electrical signal, and to output the electrical signal as an ultrasonic signal; and an image processor configured to perform a deconvolution using an estimated point spread function (PSF) with respect to the outputted ultrasonic signal in order to generate an image. The estimated PSF is obtained by using at least one measured two-dimensional PSF with respect to at least one situational variable which relates to the ultrasonic signal.

The estimated PSF may be obtained by using the at least one measured two-dimensional PSF in conjunction with a phase parameter which is determined based on the at least one situational variable.

The phase parameter may be determined based on magnitude information which relates to the ultrasonic signal and a shape of the at least one measured two-dimensional PSF.

The image processor may be further configured to select the at least one measured two-dimensional PSF from among a plurality of measured two-dimensional PSFs based on the at least one situational variable, and to select the phase parameter from among a plurality of phase parameters based on the at least one situational variable.

The at least one situational variable may include at least one from among a type of the probe, a depth of the target area, and a sound velocity of the ultrasonic waves.

The ultrasonic imaging apparatus may further include a receive beamformer configured to perform beamforming upon the ultrasonic signal. The image processor may be further configured to perform the deconvolution using the estimated PSF with respect to the beamformed ultrasonic signal in order to generate the image.

The ultrasonic imaging apparatus may further include a transmit beamformer configured to transmit time-delayed signals to the probe. The probe may be further configured to use the time-delayed signals to determine a focal point toward which the ultrasonic waves are irradiated.

In yet another aspect of one or more exemplary embodiments, a method for using an ultrasonic imaging apparatus to generate an image is provided. The method includes: irradiating, by a probe of the ultrasonic imaging apparatus, ultrasonic waves toward a target area of an object; receiving, by the probe, at least one ultrasonic echo which is reflected from the target area; converting, by the probe, the received at least one ultrasonic echo into an electrical signal; outputting, by the probe, the electrical signal as an ultrasonic signal; estimating, by an image processor, a point spread function (PSF) with respect to the outputted ultrasonic signal; and performing, by the image processor, a deconvolution using the estimated PSF with respect to the outputted ultrasonic signal in order to generate the image. The estimating the PSF includes using at least one measured two-dimensional PSF with respect to at least one situational variable which relates to the ultrasonic signal.

The estimating the PSF may further include determining a phase parameter based on the at least one situational variable, and using the at least one measured two-dimensional PSF in conjunction with the determined phase parameter.

The determining the phase parameter may include using magnitude information which relates to the ultrasonic signal and a shape of the at least one measured two-dimensional PSF.

The estimating the PSF may further include selecting the at least one measured two-dimensional PSF from among a plurality of measured two-dimensional PSFs based on the at least one situational variable. The determining the phase parameter may include selecting the phase parameter from among a plurality of phase parameters based on the at least one situational variable.

The at least one situational variable may include at least one from among a type of the probe, a depth of the target area, and a sound velocity of the ultrasonic waves.

The method may further include performing, by a receive beamformer, beamforming upon the ultrasonic signal. The performing the deconvolution may include using the estimated PSF with respect to the beamformed ultrasonic signal in order to generate the image.

The method may further include transmitting, by a transmit beamformer, time-delayed signals to the probe. The irradiating the ultrasonic waves may include using the time-delayed signals to determine a focal point toward which the ultrasonic waves are irradiated, Therefore, by acquiring a PSF and a phase parameter for an input signal based on a situational variable in order to generate a database, the ultrasonic imaging apparatus may quickly estimate a PSF for an input signal by using a PSF and a phase parameter which are selected from the database.

Further, because the PSF is estimated based on information which relates to the magnitude and phase of the input signal, the estimated PSF may have a relatively high accuracy.

BRIEF DESCRIPTION OF THE DRAWINGS

The patent or application file contains at least one drawing executed in color. Copies of this patent or patent application publication with color drawing(s) will be provided by the Office upon request and payment of the necessary fee. These and/or other aspects will become apparent and more readily appreciated from the following description of exemplary embodiments, taken in conjunction with the accompanying drawings of which.

DETAILED DESCRIPTION

Figure 1:
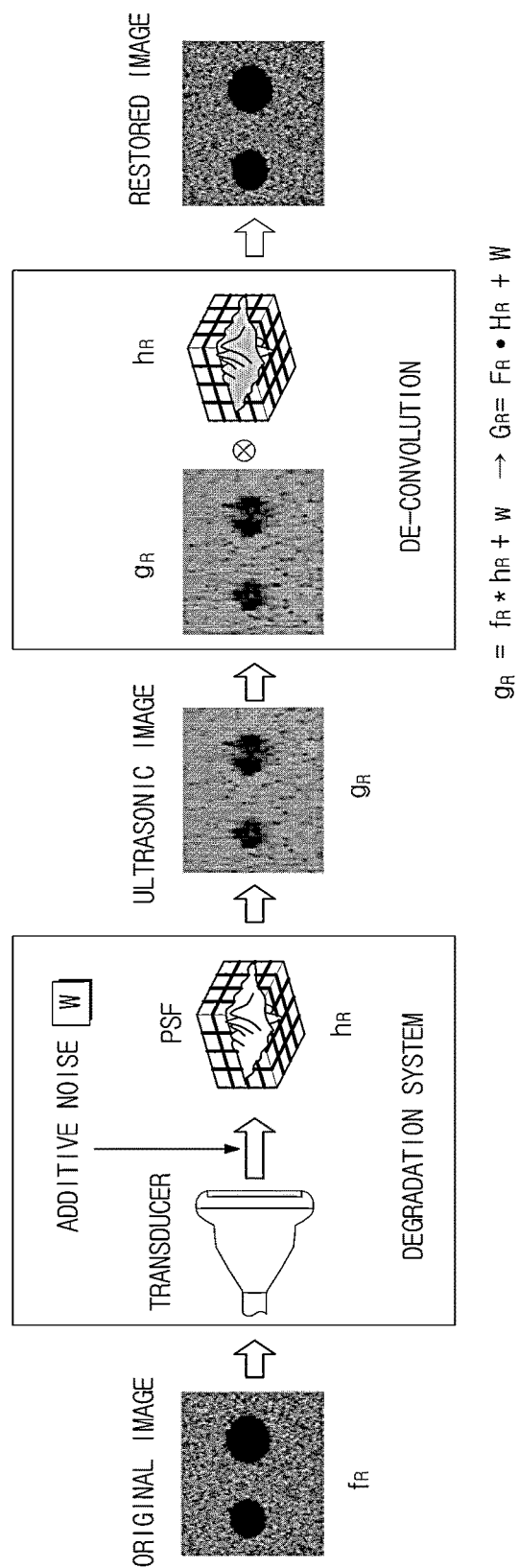
FIG. 1 is a view which illustrates a relationship between an original image of a target area of an object, an ultrasonic image of the target area, and a restored image which is restored from the ultrasonic image.

Reference will now be made in detail to exemplary embodiments, examples of which are illustrated in the accompanying drawings, wherein like reference numerals refer to like elements throughout.

Hereinafter, exemplary embodiments of an ultrasonic imaging apparatus and a control method thereof will be described with reference to the accompanying drawings.

In general, an ultrasonic imaging apparatus acquires an ultrasonic image of a target area via a probe. Then, the ultrasonic imaging apparatus estimates a Point Spread Function (PSF) from the acquired ultrasonic image, and deconvolves the estimated PSF with respect to the ultrasonic image in order to acquire a restored image that looks similar to an original image of the target area. A relationship between the original image, the ultrasonic image, and the restored image will be described in more detail with reference to FIG. 1, below.

FIG. 1 is a view which illustrates a relationship between an original image of a target area of an object, an ultrasonic image of the target area, and a restored image which is restored from the ultrasonic image.

In FIG. 1, an original image $f_R$, an ultrasonic image $g_R$, and a restored image $h_R$ are illustrated. The original image $f_R$ is an ideal image of a target area of an object. The ultrasonic image $g_R$ is an image which is acquired by using a probe of an ultrasonic imaging apparatus. The ultrasonic image $g_R$ may correspond to a beamformed ultrasonic signal. A beamformed ultrasonic signal may be acquired by irradiating ultrasonic waves toward a target area of an object, converting an ultrasonic signal (hereinafter, referred to as an ultrasonic echo) which is reflected from the target area into an electrical signal in order to acquire an ultrasonic signal, and beamforming the ultrasonic signal. The restored image $h_R$ is an image which is restored from the ultrasonic image $g_R$ such that the image looks similar to the original image $f_R$.

Referring to FIG. 1, the ultrasonic image $g_R$ which is acquired via the probe has blurred edges and noise. The reason that the ultrasonic image $g_R$ is different from the original image $f_R$ is because the quality of an original image is degraded and noise is added to the original image due to the physical properties of the probe when an ultrasonic image is acquired via the probe. Presently, a relationship between the original image $f_R$ and the ultrasonic image $g_R$ will be described in more detail with reference to FIGS. 2A and 2B.

Figure 2A:
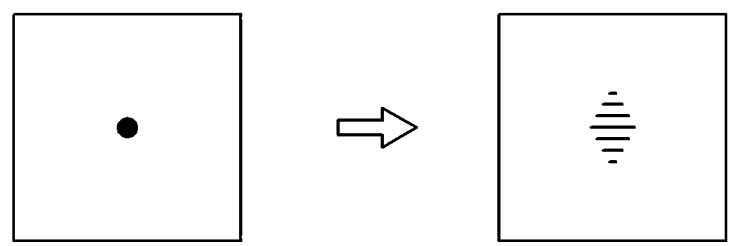
FIGS. 2A and 2B are views which illustrate a relationship between an original image and an ultrasonic image.

FIG. 2A illustrates an original image on the left side of the figure and an ultrasonic image on the right side of the figure. Referring to FIG. 2A, if a target area is represented as a dot in the original image, the target area of the ultrasonic image is represented as a shape which is spread out to the up, down, left, and right of the dot. The difference between the original image and the ultrasonic image is more significant at a deeper depth of the target area.

Figure 2B:
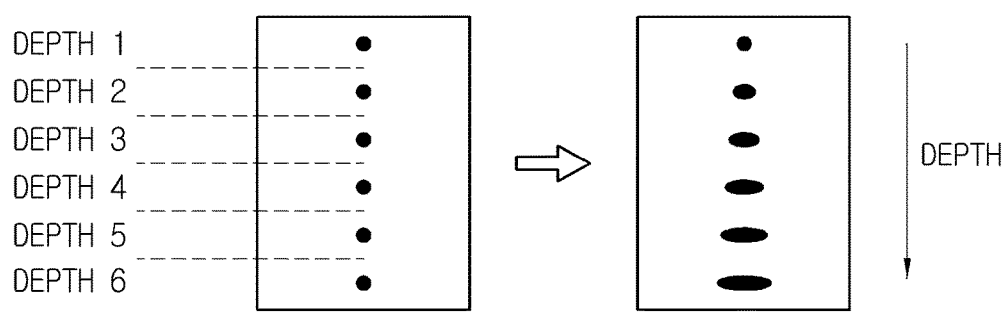

FIG. 2B illustrates an original image of target areas having different respective depths on the left side of the figure, and an ultrasonic image of the target areas on the right side of the figure. Referring to FIG. 2B, target areas which are located closer to a probe show more similar shapes as between the original image and the corresponding ultrasonic image. However, target areas which are located more distant from the probe show significantly different shapes as between the original image and the corresponding ultrasonic image.

In particular, as a result of a distance between a probe and a target area and noise, in addition to the physical properties of the probe, the quality of an original image is degraded. If such a degraded ultrasonic image is output without restoration thereof, it may be difficult to accurately diagnose a target area. Accordingly, in order to increase an accuracy of a diagnosis, it is important to restore an ultrasonic image such that the restored image looks similar to an original image.

If a degradation model of degrading the quality of the original image $f_R$ is expressed as a PSF, the ultrasonic image $g_R$ may be obtained as the result of a convolution of the original image $f_R$ with the PSF.

A conventional ultrasonic imaging apparatus estimates a PSF from an ultrasonic image $g_R$, and deconvolves the estimated PSF with the ultrasonic image $g_R$, thereby acquiring a restored image which is similar to an original image.

In this aspect, as a PSF is more accurately estimated, a restored image which is more similar to an original image can be acquired.

A method of estimating a PSF may be classified into a method of estimating a one-dimensional (1D) PSF and a method of estimating a two-dimensional (2D) PSF.

An example of a method of estimating a 1D PSF is an Autoregressive Moving Average (ARMA). By using this method, a 1D PSF can be estimated within a relatively short time period, but the method generally has a relatively low accuracy. Accordingly, when an estimated 1D PSF is deconvolved with an ultrasonic image to acquire a restored image, the restored image has a relatively high resolution in the axial direction, but a relatively low resolution in the lateral direction.

An example of a method of estimating a 2D PSF is Cepstrum. The Cepstrum method includes converting an input signal in a time domain into a signal in a frequency domain, and then estimating a 2D PSF in the frequency domain.

The Cepstrum method may be classified into a method of estimating a 2D PSF using only magnitude information which relates to an ultrasonic image, and a method of estimating a 2D PSF using both magnitude information and phase information which relate to an ultrasonic image.

A 2D PSF which is estimated using only magnitude information which relates to an ultrasonic image has a lower accuracy than a 2D PSF estimated in consideration of both magnitude information and phase information relating to the ultrasonic image.

In particular, a 2D PSF which is estimated in consideration of both magnitude information and phase information relating to an ultrasonic image has a relatively high accuracy. However, when both magnitude information and phase information relating to an ultrasonic image are considered, complexity and computation increase. As a result, it may be difficult to estimate a 2D PSF within a short time period, and accordingly, there is a limitation in applying such a method to an ultrasonic imaging apparatus with respect to an ability to provide restored images in real time.

According to a high-speed 2D PSF estimation method, phase information is removed (minimum phase) in order to lower complexity. However, if phase information is removed, the accuracy of an estimated 2D PSF is lowered accordingly.

Hereinafter, an ultrasonic imaging apparatus which is configured for estimating a 2D PSF more rapidly and accurately than by applying the Cepstrum method, including using both magnitude information and phase information which relates to an ultrasonic image, will be described.

Figure 3:
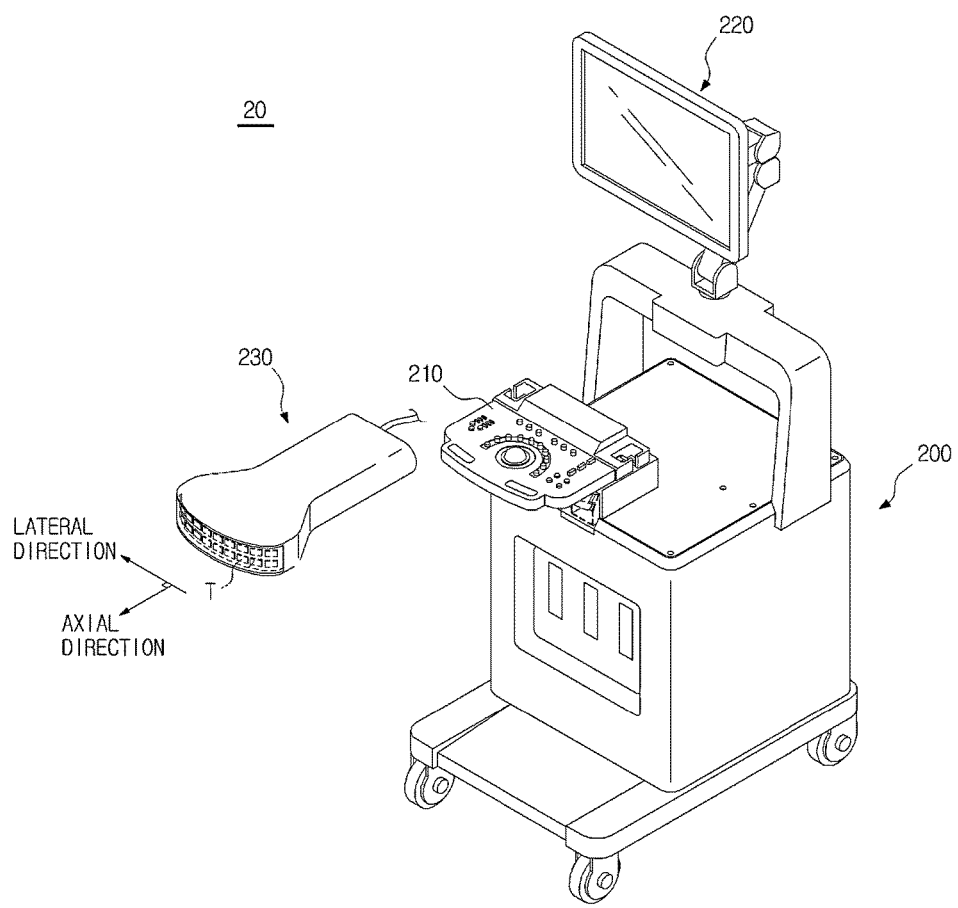
FIG. 3 is a perspective view of an ultrasonic imaging apparatus, according to an exemplary embodiment.

FIG. 3 is a perspective view of an ultrasonic imaging apparatus, according to an exemplary embodiment.

Referring to FIG. 3, an ultrasonic imaging apparatus 20 may include a main body 200, an input unit (also referred to herein as an "input device") 210, a display unit (also referred to herein as a "display" and/or as a "display device") 220, and a probe 230.

The main body 200 accommodates main components of the ultrasonic imaging apparatus 20. For example, referring to FIG. 4, the main body 200 may accommodate a controller 240, a transmit beamformer 250, a receive beamformer 260, an image producer (also referred to herein as an "image generator") 270, and a PSF database 280. The individual components will be described in more detail with reference to FIG. 4 below.

The input unit 210 facilitates an input, by an operator, of an instruction or a command for manipulating the ultrasonic imaging apparatus 20. For example, the operator may input one or more of a diagnosis start command, a command for selecting an area to be diagnosed, a command for selecting a diagnosis type, and/or a command for selecting a mode for an ultrasonic image to be finally output, via the input unit 210. The input unit may include at least one of a keyboard, a mouse, a trackball, a touch screen, a foot switch, and a foot pedal.

For example, the keyboard may be implemented as hardware, and mounted on the upper part of the main body 200. The keyboard may include at least one(s) of a switch(es), a key(s), a wheel, a joystick, a trackball, and a knob. The foot switch or the foot pedal may be disposed below the main body 200. The operator may control a subset of functions of the ultrasonic imaging apparatus 200 by using the foot pedal.

As another example, the keyboard may be implemented as software, such as a Graphic User Interface (GUI). A keyboard which is implemented as software may be displayed via the display unit 220.

The display unit 220 may display a restored image. There may be provided a plurality of display units. The display unit 220 may have only a display function, or may have both a display function and an input function. If the display unit 220 includes a touch screen, the display unit 220 may have both a display function and an input function.

Figure 4:
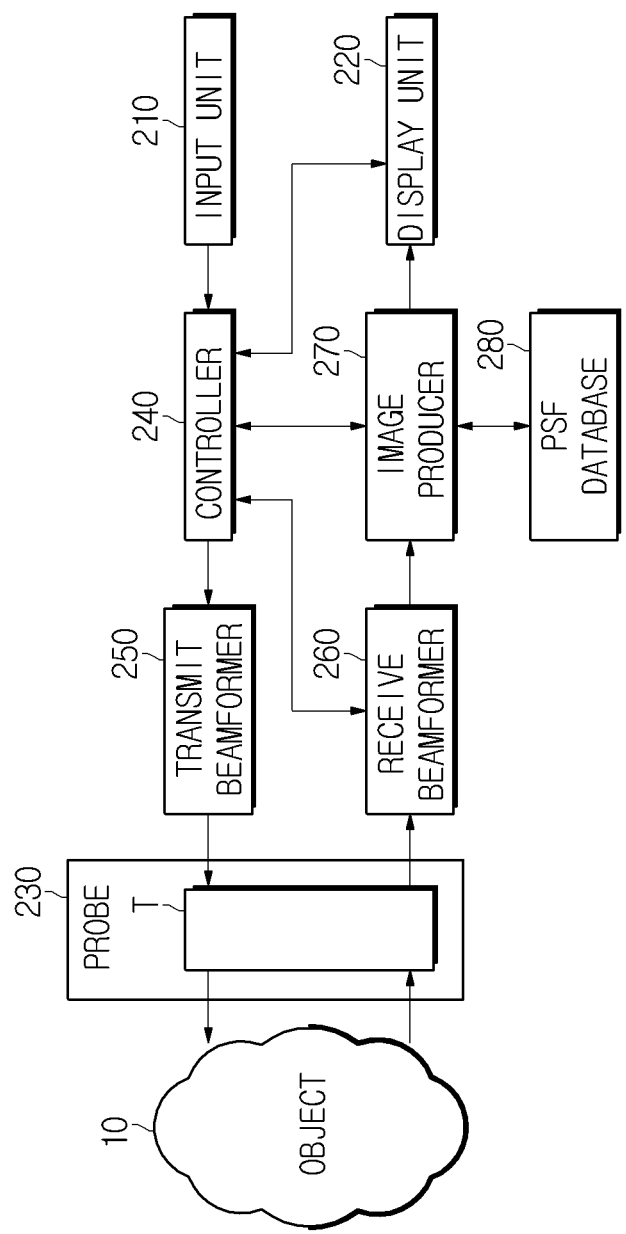
FIG. 4 is a block diagram of an ultrasonic imaging apparatus, according to an exemplary embodiment.

The probe 230 contacts an object 10 (see FIG. 4). One or more ultrasonic elements T are installed in one end of the probe 230. The ultrasonic elements T irradiate ultrasonic waves toward the inside of the object 10, receive at least one ultrasonic echo which is reflected from the inside of the object 10, and convert the received at least one ultrasonic echo into an electrical signal. For example, each ultrasonic element T may include an ultrasonic generator which is configured to generate ultrasonic waves and an ultrasonic reception device which is configured to receive at least one ultrasonic echo and convert the received at least one ultrasonic echo into an electrical signal. As another example, the ultrasonic element T itself may be configured to generate ultrasonic waves and to receive ultrasonic echoes.

The ultrasonic elements T may include ultrasonic transducers. A transducer is a device which is configured to convert a specific type of energy into another type of energy. For example, the ultrasonic transducer may convert electricity energy into wave energy, or wave energy into electricity energy. In particular, the ultrasonic transducers T may perform all functions of an ultrasonic generator and an ultrasonic receiver.

In more detail, the ultrasonic transducers T may include a piezoelectric material and/or a piezoelectric thin film. If alternating current power from an external power supply or from an internal power storage unit, such as, for example, a battery, is applied to the piezoelectric material or the piezoelectric thin film, the piezoelectric material or the piezoelectric thin film vibrates at a specific frequency so that a specific frequency of ultrasonic waves are generated according to the vibration frequency. Further, if an ultrasonic echo having a specific frequency arrives at the piezoelectric material or the piezoelectric thin film, the piezoelectric material or the piezoelectric thin film vibrates according to the frequency of the ultrasonic echo. As a result, the piezoelectric material or the piezoelectric thin film outputs alternating current which corresponds to the vibration frequency.

Each ultrasonic transducer T may include a magnetostrictive ultrasonic transducer which uses the magnetostrictive effect of a magnetic material, a piezoelectric ultrasonic transducer which uses the piezoelectric effect of a piezoelectric material, or a capacitive micromachined ultrasonic transducer (CMUT) that transmits and receives ultrasonic waves by using vibrations of several hundreds or thousands of micromachined thin films. However, the ultrasonic transducer T may include any other type ultrasonic transducer which is capable of generating ultrasonic waves based on electrical signals or generating electrical signals based on ultrasonic waves.

The ultrasonic transducers T may be arranged in a linear array or in a convex array at the end part of the probe 230. In this case, the ultrasonic transducers T may be arranged in a line or in a matrix form. If the ultrasonic transducers T are arranged in a line, by moving the probe 230 in a scan direction, a plurality of ultrasonic images may be acquired. If the ultrasonic transducers are arranged in a matrix form, by transmitting ultrasonic waves simultaneously, a plurality of ultrasonic images may be acquired.

Although not shown in the drawings, a cover for covering the ultrasonic transducers T may be provided.

FIG. 4 is a block diagram of an ultrasonic imaging apparatus, according to an exemplary embodiment.

Referring to FIG. 4, an ultrasonic imaging apparatus 20 may include an input unit 210, a display unit 220, a controller 240, a transmit beamformer 250, a probe 230, a receive beamformer 260, an image producer 270, and a PSF database 280.

The input unit 210, the display unit 220, and the probe 230 have been described above with reference to FIG. 3, and accordingly, further descriptions thereof will be omitted.

The controller 240 may control overall operations of the ultrasonic imaging apparatus 20. In detail, the controller 240 may generate a control signal for controlling at least one of the transmit beamformer 250, the receive beamformer 260, the image producer 270, and the display unit 220, based on an instruction and/or a command which is received via the input unit 210. Further, the controller 240 may generate a control signal for controlling individual components based on an instruction and/or a command which is received from an external device via wired and/or wireless communication.

The PSF database 280 may store at least one PSF. The at least one PSF may include a 2D PSF which is actually measured based on at least one situational variable. The situational variable may include at least one of a type of a probe, a distance (that is, a depth of a target area) between the probe and the target area, and a sound velocity of ultrasonic waves.

Figure 5:
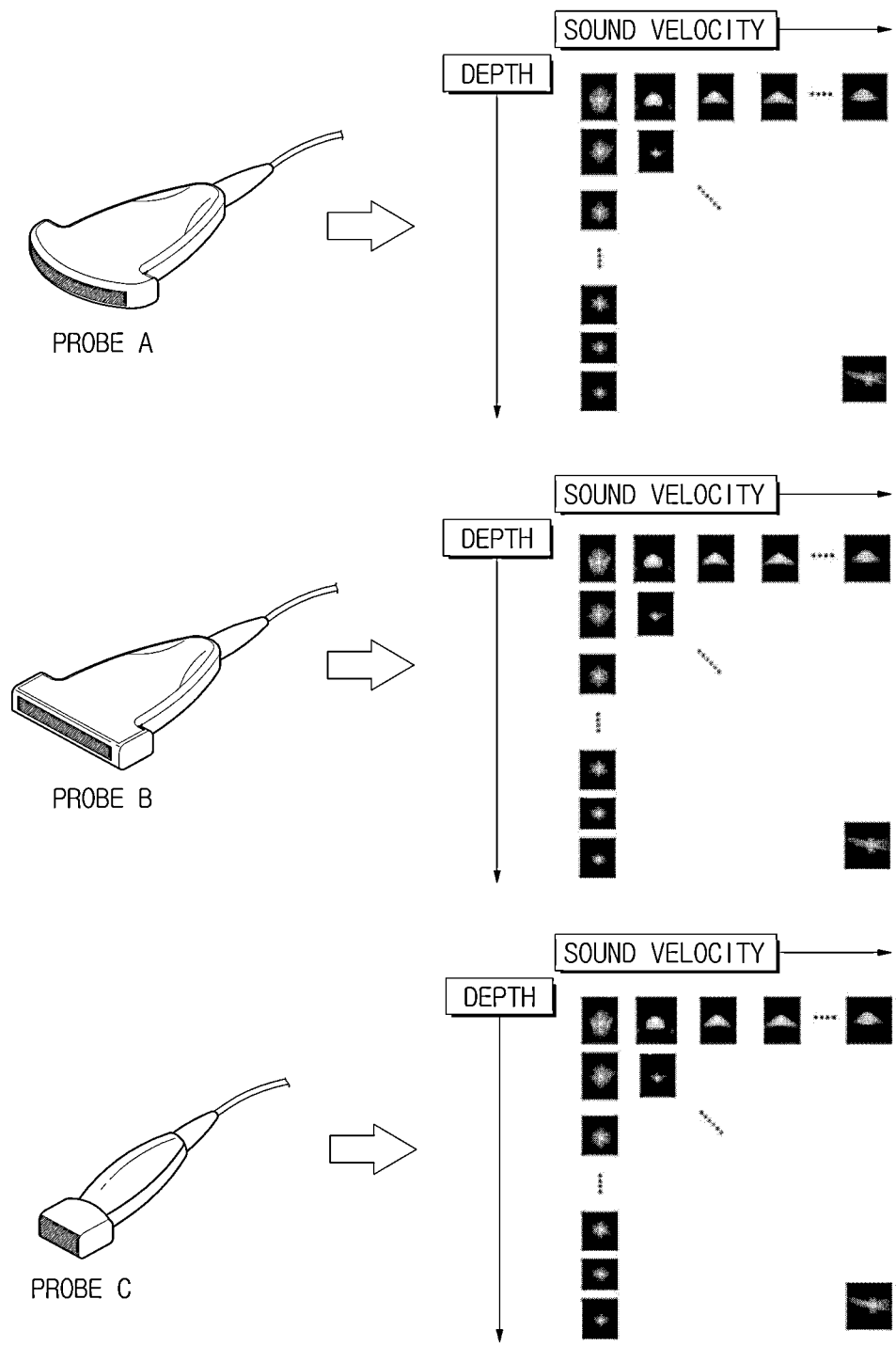
FIG. 5 is a view which illustrates an exemplary embodiment of a Point Spread Function (PSF) database.

FIG. 5 is a view which illustrates an exemplary embodiment of the PSF database 280. In FIG. 5, a case in which the PSF database 280 stores 2D PSFs which are actually measured based on situational variables, such as a type of a probe, a depth of a target area, and/or a sound velocity, is illustrated.

According to an exemplary embodiment, the PSF database 280 may store phase parameters which are determined in advance based on the situational variables, in addition to the 2D PSFs which are actually measured based on the situational variables. The phase parameters are obtained by parameterizing phase information which is usable for estimating new 2D PSFs based on 2D PSFs which are selected from the PSF database 280.

In order to determine phase parameters, first, a 2D PSF is estimated based on magnitude information which relates to an ultrasonic image. Then, the shape of the estimated 2D PSF is compared to the shapes of actually measured 2D PSFs while varying values of factors which represent phase information relating to the estimated 2D PSF. Then, values of factors which correspond to when the shape of the estimated 2D PSF is most similar to the shape of an actually measured 2D PSF are determined as phase parameters.

A method of determining phase parameters will be described in more detail below. For example, an ultrasonic image of a target area which is located at a depth of 5 cm from a surface of an object is acquired by using a "probe A". Then, a 2D PSF is estimated from the ultrasonic image, and the shape of the estimated 2D PSF is compared to the shapes of actually measured 2D PSFs while varying values of factors which represent phase information relating to the estimated 2D PSF. Values of factors which correspond to when the shape of the estimated 2D PSF is most similar to the shape of an actually measured 2D PSF are determined as phase parameters in correspondence with a case in which situational variables are a "probe A" and a "target area depth of 5 cm".

By applying the above-described method to all situational variables, phase parameters for the respective situational variables are determined. For example, phase parameters may be determined based on a type of a probe and a depth of a target area. The determined phase parameters may be stored in the PSF database 280.

Referring again to FIG. 4, the transmit beamformer 250 may perform transmit beamforming. The transmit beamforming is performed in order to focus ultrasonic waves from one or more ultrasonic elements T onto a focal point. In particular, the transmit beamforming is performed in order to cause the ultrasonic elements T to generate ultrasonic waves in an appropriate order in order to compensate for time differences with which ultrasonic waves generated from the ultrasonic elements T arrive at the focal point. The transmit beamforming will be described in more detail with reference to FIG. 6 below.

Figure 6:
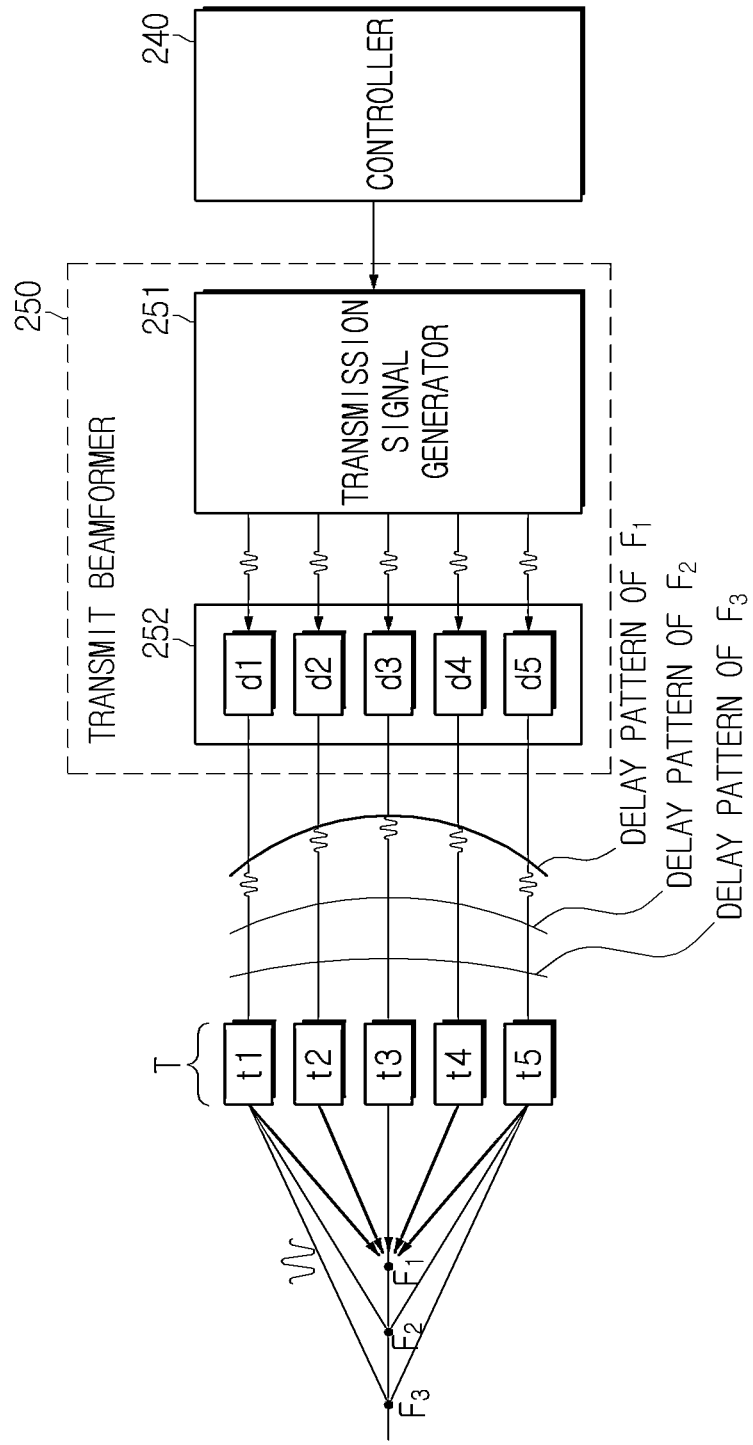
FIG. 6 illustrates a configuration of a transmit beamformer of an ultrasonic imaging apparatus.

FIG. 6 illustrates a configuration of the transmit beamformer 250. As illustrated in FIG. 6, the transmit beamformer 250 may include a transmission signal generator 251 and a time delay unit (also referred to herein as a "time delay component" and/or as a "time delay device") 252.

The transmission signal generator 251 may generate transmission signals (such as, for example, high-frequency alternating current signals) that are to be applied to the ultrasonic elements T, based on a control signal which is received from the controller 240. The transmission signals generated by the transmission signal generator 251 are provided to the time delay unit 252.

The time delay unit 252 may delay the transmission signals generated by the transmission signal generator 251 in order to adjust a time at which each transmission signal arrives at the corresponding ultrasonic element T. If the transmission signals delayed by the time delay unit 252 are applied to the ultrasonic elements T, the ultrasonic elements T generate ultrasonic waves which respectively correspond to the frequencies of the transmission signals. The ultrasonic waves generated by the ultrasonic elements T are focused onto a focal point. The location of the focal point onto which the ultrasonic waves generated by the ultrasonic elements T are focused depends on what delay pattern has been applied to the transmission signals.

In more detail, in the exemplary embodiment of FIG. 6, five ultrasonic elements t1, t2, t3, t4, and t5 are provided, and three delay patterns that can be applied to transmission signals are represented as thick solid lines, medium solid lines, and thin solid lines, respectively.

When the delay pattern represented as the thick solid lines is applied to transmission signals generated by the transmission signal generator 251, ultrasonic waves generated by the ultrasonic elements t1 to t5 are focused onto a first focal point $F_1$.

When the delay pattern represented as the medium solid lines is applied to transmission signals generated by the transmission signal generator 251, ultrasonic waves generated by the ultrasonic elements t1 to t5 are focused onto a second focal point $F_2$ which is more distant than the first focal point $F_1$.

When the delay pattern represented as the thin solid lines is applied to transmission signals generated by the transmission signal generator 251, ultrasonic waves generated by the ultrasonic elements t1 to t5 are focused onto third focal point $F_3$ which is more distant than the second focal point $F_2$.

As described above, the location of a focal point varies based on what type of delay pattern is applied to transmission signals generated by the transmission signal generator 251. Accordingly, when a delay pattern is applied, ultrasonic waves that are to be applied to an object are focused onto a fixed focal point (i.e., "fixed-focusing"). However, when two or more different delay patterns are applied, ultrasonic waves that are to be applied to an object are focused onto several focal points (i.e., "multi-focusing").

As such, ultrasonic waves generated by the individual ultrasonic elements T are fixed-focused onto a single focal point, or multi-focused onto several focal points. The focused ultrasonic waves are directed to the inside of an object. The ultrasonic waves directed to the inside of the object are reflected from a target area of the object. At least one ultrasonic echo which is reflected from the target area is received by the ultrasonic elements T. Then, the ultrasonic elements T convert the received at least one ultrasonic echo into electrical signals. Hereinafter, the converted electrical signals will be simply referred to as ultrasonic signals. The ultrasonic signals output from the ultrasonic elements T are amplified and filtered, then converted into digital signals, and provided to the receive beamformer 260.

Referring again to FIG. 4, the receive beamformer 260 may perform receive beamforming on the ultrasonic signals which have been converted into the digital signals. The receive beamforming is performed in order to correct time differences between ultrasonic signals output from individual ultrasonic elements and then to focus the corrected signals. The receive beamforming will be described in more detail with reference to FIG. 7 below.

Figure 7:
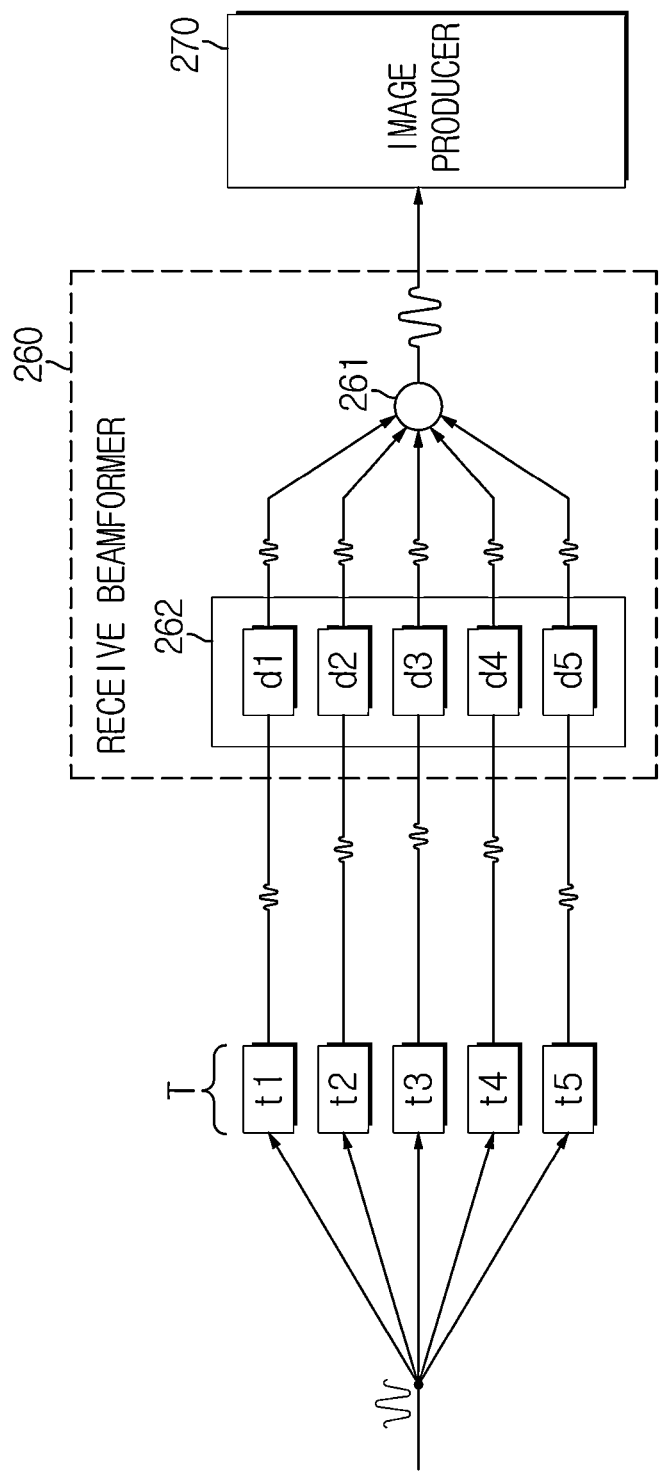
FIG. 7 illustrates a configuration of a receive beamformer of an ultrasonic imaging apparatus.

FIG. 7 is a block diagram of the receive beamformer 260, according to an exemplary embodiment. Referring to FIG. 7, the receive beamformer 260 may include a time-difference corrector 262 and a focusing unit (also referred to herein as a "focuser" and/or as a "focus device") 261.

The time-difference corrector 262 delays respective ultrasonic signals from the individual ultrasonic elements T by predetermined time periods so that the ultrasonic signals can be transferred to the focusing unit 261 at the same time.

The focusing unit 261 may focus the ultrasonic signals which have been subjected to time-difference correction by the time-difference corrector 262. In particular, the focusing unit 261 may focus the ultrasonic signals after allocating a predetermined weight (for example, a beamforming coefficient) to each ultrasonic signal in order to enhance or attenuate the corresponding ultrasonic signal vis-a-vis the other ultrasonic signals. The focused ultrasonic signal may be provided to the image producer 270.

Referring again to FIG. 4, the image producer 270 may select at least one 2D PSF and at least one phase parameter from the PSF database 280 based on an ultrasonic signal, and estimate a 2D PSF based on the selected 2D PSF and based on the selected phase parameter. The image producer 270 will be described in more detail with reference to FIG. 8 below.

Figure 8:
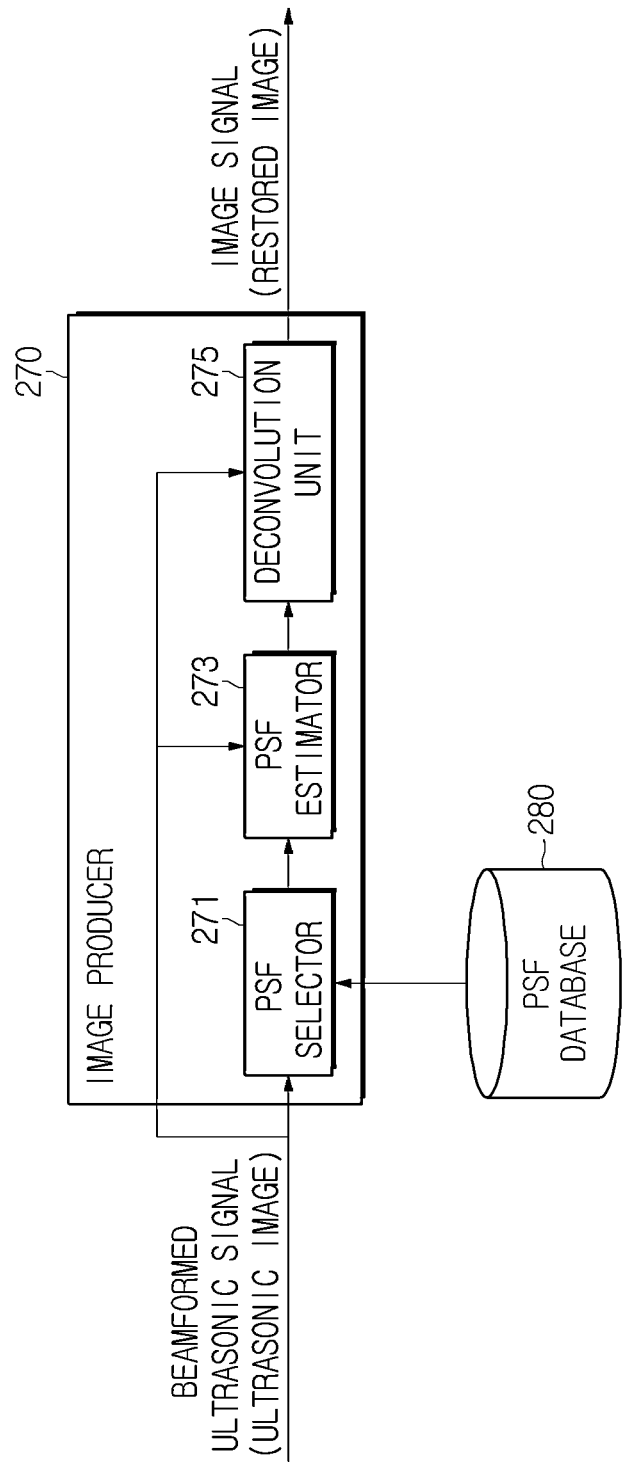
FIG. 8 is a block diagram of an image producer, according to an exemplary embodiment.

FIG. 8 is a block diagram of the image producer 270, according to an exemplary embodiment.

Referring to FIG. 8, the image producer 270 may include a PSF selector 271, a PSF estimator 273, and a deconvolution unit (also referred to herein as a "deconvolver", a "deconvolution component", and/or a "deconvolution device") 275.

The PSF selector 271 selects at least one 2D PSF and at least one phase parameter from the PSF database 280, based on a situational variable of a beamformed ultrasonic signal. For example, if it is determined that the beamformed ultrasonic signal has been acquired by using a probe A, and a target area is located at a depth of 1 (see FIG. 2B), based on the results of an analysis which has been performed on the beamformed ultrasonic signal, the PSF selector 271 selects a 2D PSF and a phase parameter which correspond to the depth of 1 from the PSF database 280. If it is determined that the beamformed ultrasonic signal has been acquired by using a probe A, and target areas are respectively located at depths of 3 and 5 (see FIG. 2B), based on the results of an analysis which has been performed on the beamformed ultrasonic signal, the PSF selector 271 selects a 2D PSF and a phase parameter which correspond to the depth of 3, and also selects a 2D PSF and a phase parameter which correspond to the depth of 5, from the PSF database 280.

The PSF estimator 273 estimates a 2D PSF using at least one 2D PSF and at least one phase parameter selected by the PSF selector 271. The reason for again estimating a 2D PSF is because a situational variable which relates to an actually measured 2D PSF may be different from a situational variable which relates to an ultrasonic signal that is acquired during actual diagnosis.

For example, sound velocity may vary as between individual persons, even at the same depth of a target area. Accordingly, although 2D PSFs are actually measured based on a type of a probe, a depth of a target area, and sound velocity in order to generate and populate the PSF database 280, there may occur a case in which a PSF stored in the PSF database 280 cannot be used, due to changes of situational variables during actual ultrasonography. In this case, if a PSF which corresponds to situational variables which relate to a situation most similar to an actual diagnosis situation is selected, and a 2D PSF is estimated based on the selected PSF, a 2D PSF can be more rapidly estimated. Further, because the 2D PSF is estimated using a predetermined phase parameter, the accuracy of the estimated 2D PSF can be improved.

If a situational variable of the actually measured 2D PSF is identical to the situational variable of the ultrasonic signal acquired during actual diagnosis, a PSF which corresponds to the situational variable of the ultrasonic signal is selected from the PSF database 280, and the beamformed ultrasonic signal is deconvolved with the selected PSF.

The deconvolution unit 275 deconvolves the beamformed ultrasonic signal using the estimated 2D PSF. As a result, an image which is very similar to an original image is acquired. The acquired image may be subject to postprocessing and then displayed as an image via the display unit 220.

Figure 9:
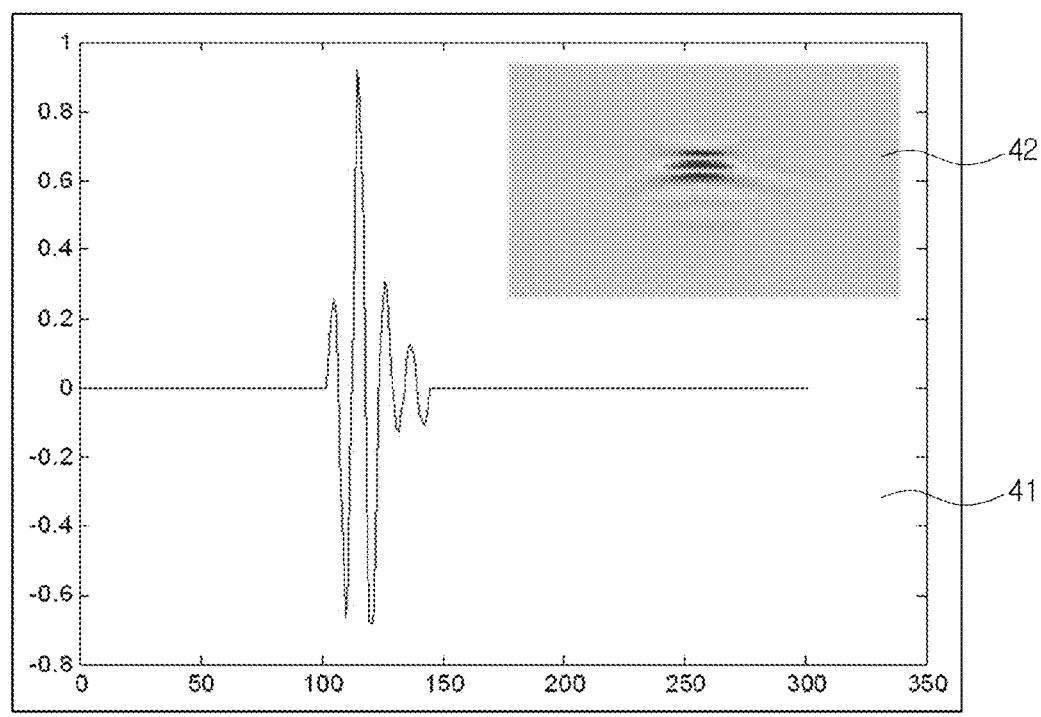
FIG. 9 illustrates a one-dimensional (1D) PSF and a two-dimensional (2D) PSF which are actually measured for a beamformed ultrasonic signal.

FIG. 9 illustrates a 1D PSF 41 and a 2D PSF 42 which are actually measured based on a situational variable.

Figure 10:
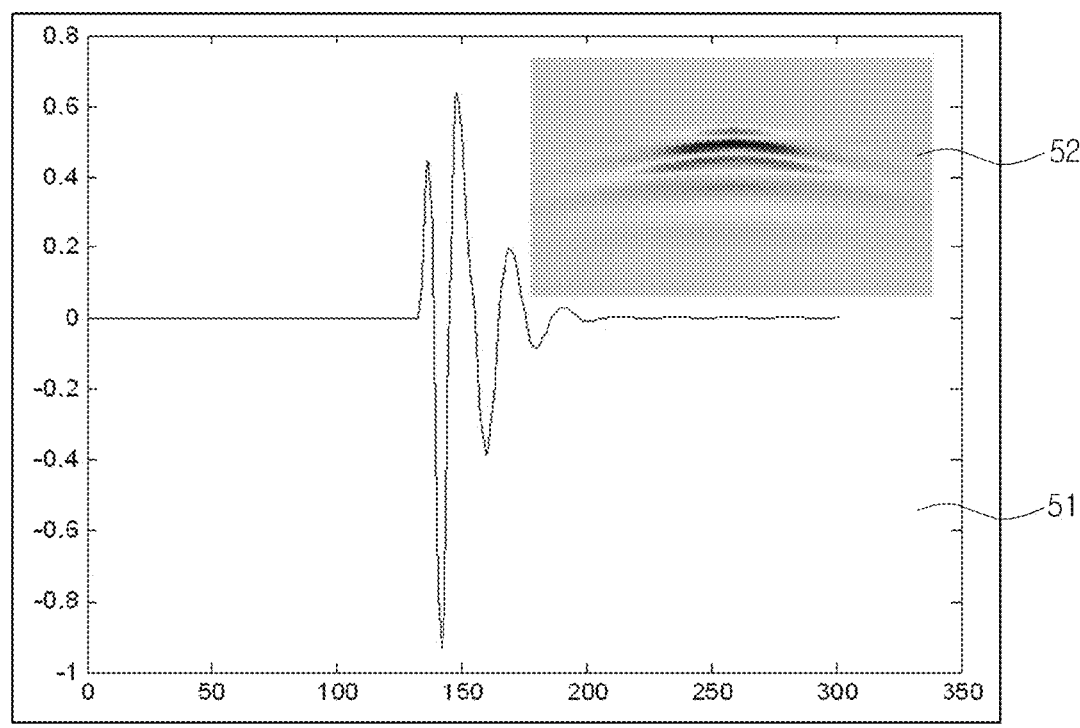
FIG. 10 illustrates a 1D PSF and a 2D PSF which are estimated for a beamformed ultrasonic signal, based on information which relates to a magnitude of the beamformed ultrasonic signal, without considering information which relates to a phase of the beamformed ultrasonic signal.

FIG. 10 illustrates an estimated 1D PSF 51 and an estimated 2D PSF 52. The 2D PSF 52 has been estimated based on the Cepstrum method. In particular, the 2D PSF 52 has been estimated based on magnitude information after removing phase information (minimum phase). The shape of the 2D PSF 52 illustrated in FIG. 10 is significantly different from the shape of the actually measured 2D PSF 42 illustrated in FIG. 9.

Figure 11:
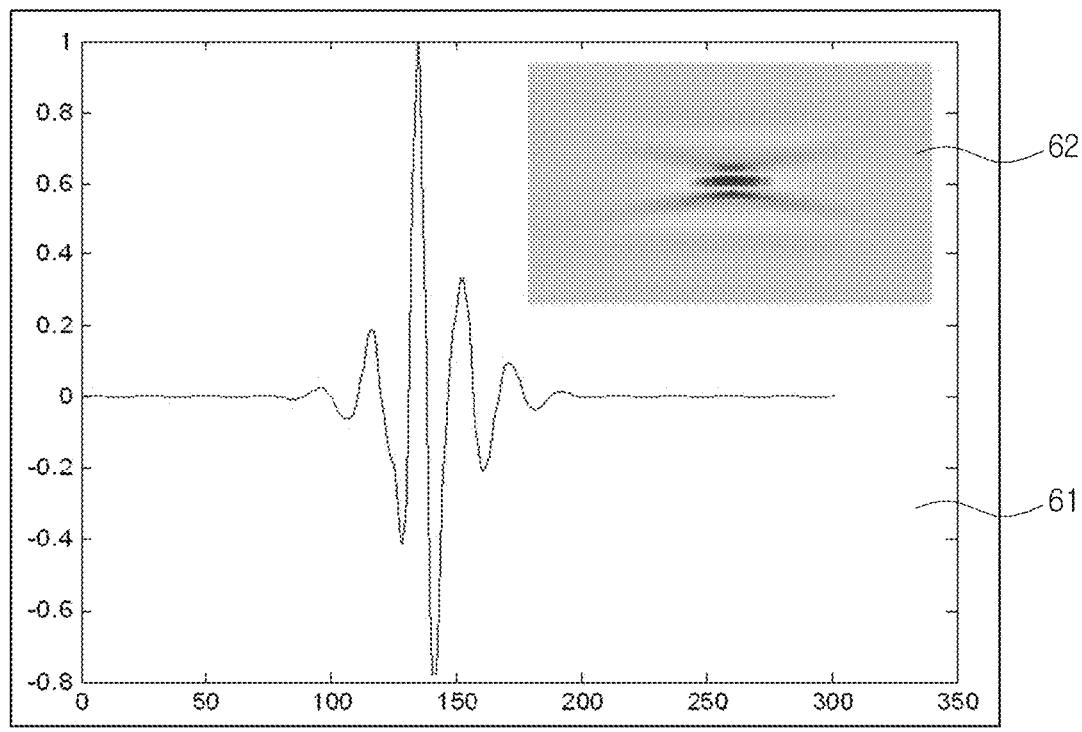
FIG. 11 illustrates a 1D PSF and a 2D PSF which are estimated for a beamformed ultrasonic signal, based on a predetermined phase parameter and information which relates to a magnitude of the beamformed ultrasonic signal.

FIG. 11 illustrates an estimated 1D PSF 61 and an estimated 2D PSF 62. The 2D PSF 62 has been estimated based on the Cepstrum method, based on magnitude information and a phase parameter. The shape of the 2D PSF 62 illustrated in FIG. 11 is similar to the shape of the actually measured 2D PSF 42 illustrated in FIG. 9.

Figure 12:
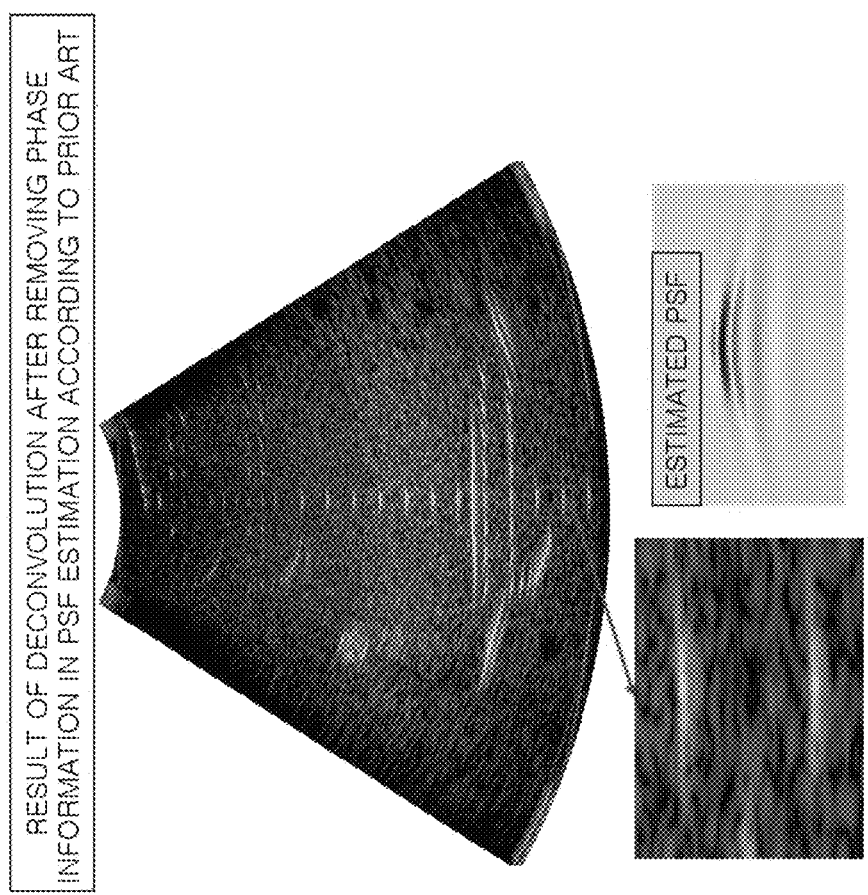
FIG. 12 is a view which illustrates a comparison between an original image and the result of a deconvolution which is performed using a 2D PSF which is estimated based on information which relates to a magnitude of a beamformed ultrasonic signal.
Figure 12:
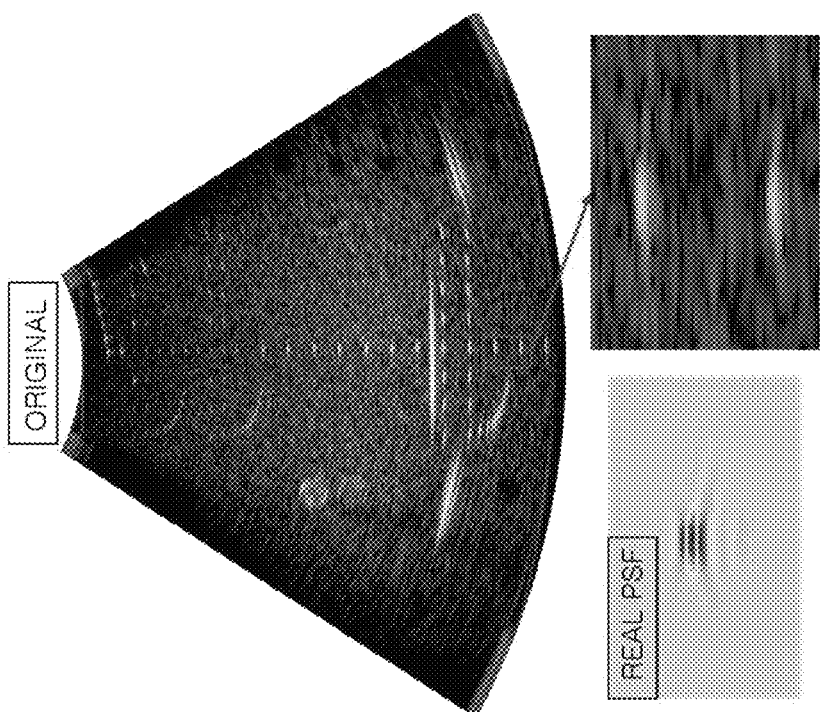

FIG. 12 is a view which illustrates a comparison between an original image (left side of figure) and a result of a deconvolution (right side of figure) which is performed using a 2D PSF which is estimated based on magnitude information. Referring to FIG. 12, it is seen that the result of the deconvolution has spread out in the lateral direction although it maintains picture quality in the axial direction, as compared with the original image. The reason for this phenomenon is that the shape of the estimated 2D PSF is similar to the shape of an actually-measured 2D PSF in the axial direction, but is significantly different from the shape of the actually-measured 2D PSF in the lateral direction.

Figure 13:
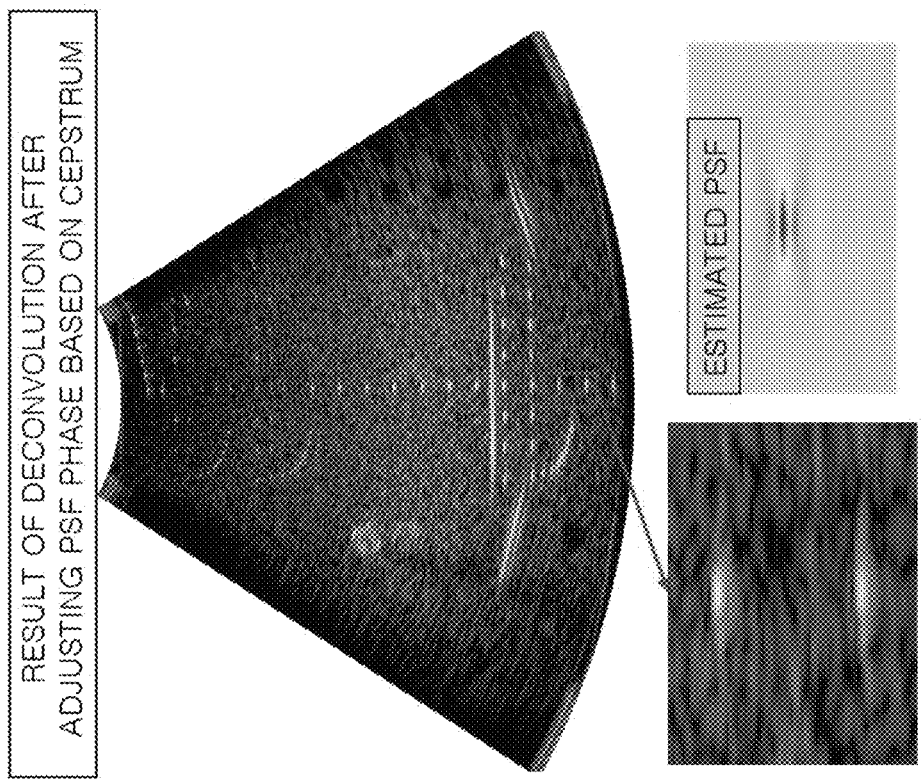
FIG. 13 is a view which illustrates a comparison between an original image and the result of a deconvolution which is performed using a 2D PSF which is estimated based on information which relates to a magnitude of a beamformed ultrasonic signal and phase information which is set to a default value.
Figure 13:
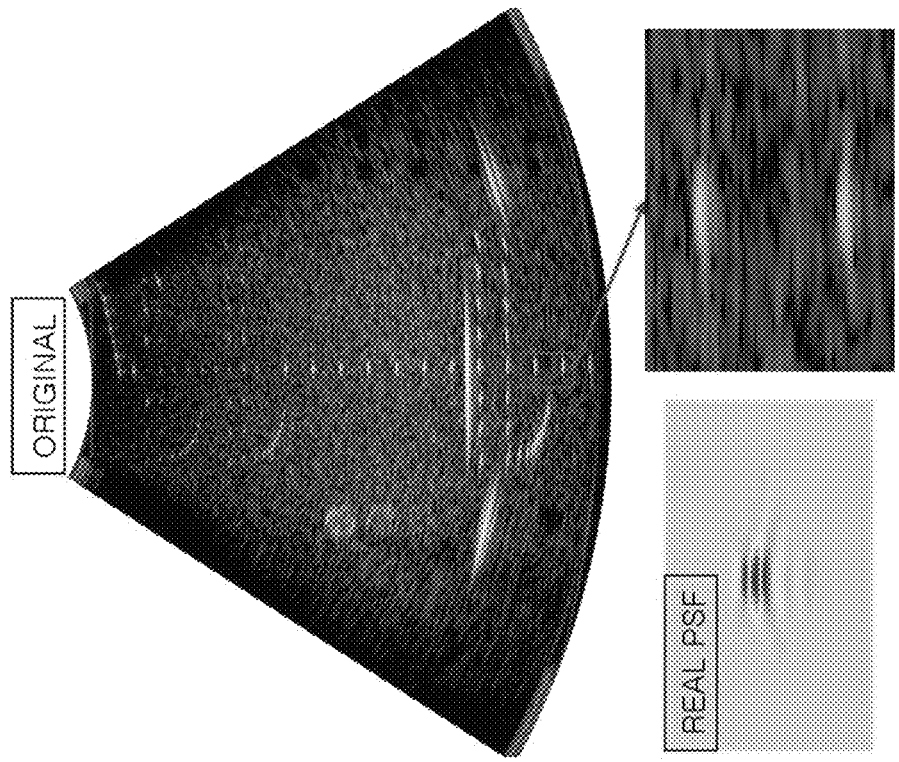

FIG. 13 is a view which illustrates a comparison between an original image (left side of figure) and a result of a deconvolution (right side of figure) which is performed using a 2D PSF which is estimated based on magnitude information and phase information which is set to a default value. Referring to FIG. 13, it is seen that the result of the deconvolution has a relatively small amount spread out in the axial direction although it maintains picture quality in the lateral direction, as compared with the original image. The reason for this phenomenon is that the shape of the estimated 2D PSF is similar to the shape of an actually-measured 2D PSF in the lateral direction, but is only slightly different from the shape of the actually-measured 2D PSF in the axial direction.

Figure 14:
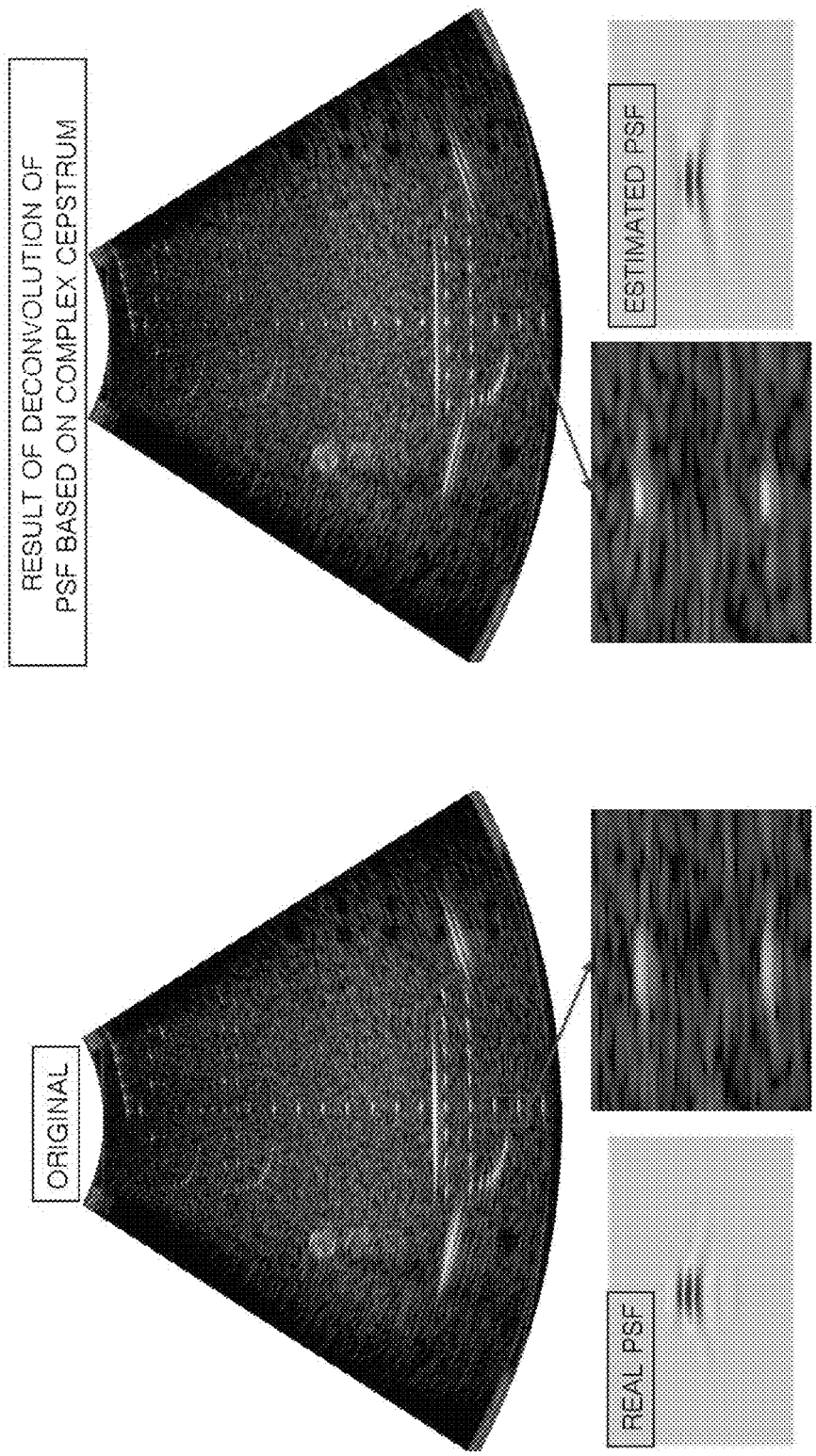
FIG. 14 is a view which illustrates a comparison between an original image and the result of a deconvolution which is performed using a 2D PSF which is estimated based on a predetermined phase parameter and information which relates to a magnitude of a beamformed ultrasonic signal.

FIG. 14 is a view which illustrates a comparison between an original image (left side of figure) and a result of a deconvolution (right side of figure) which is performed using a 2D PSF which is estimated based on magnitude information and a phase parameter. Referring to FIG. 14, it is seen that the shape of the estimated 2D PSF is nearly similar to the shape of an actually-measured 2D PSF both in the lateral direction and in the axial direction. As a result, the result of the deconvolution is similar to the original image.

Figure 15:
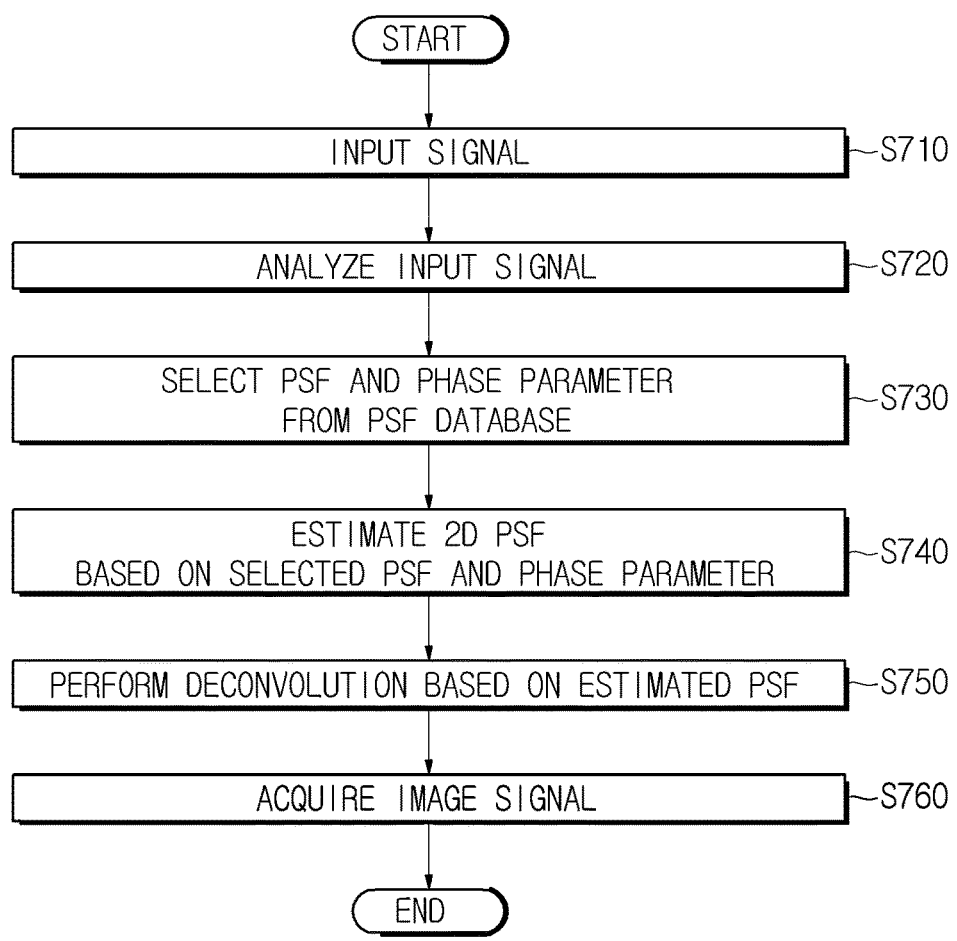
FIG. 15 is a flowchart which illustrates a control method which is executable by an ultrasonic imaging apparatus, according to an exemplary embodiment.

FIG. 15 is a flowchart which illustrates a control method which is executable by an ultrasonic imaging apparatus, according to an exemplary embodiment.

If an input signal is input in operation S710, then in operation S720, the input signal is analyzed. The input signal may include a beamformed ultrasonic signal. The input signal may be analyzed based on a situational variable. The situational variable may include at least one from among a type of a probe, a depth of a target area, and a sound velocity.

If the input signal is analyzed, then in operation S730, at least one PSF and at least one phase parameter are selected from the PSF database 280 (see FIG. 4) based on the result of the analysis. In particular, a 2D PSF may be selected. Alternatively, one or more 2D PSFs may be selected. The phase parameter may include a parameter which is determined in advance based on the situational variable. For example, the phase parameter may be determined based on a depth of a target area.

If the PSF and the phase parameter are selected, then in operation S740, a 2D PSF may be estimated based on the selected PSF and the determined phase parameter. As such, if a 2D PSF is estimated based on a selected PSF and a phase parameter, the accuracy of the estimated 2D PSF may increase, because both magnitude information and phase information are considered.

If the 2D PSF is estimated, then in operation S750, the estimated 2D PSF is deconvolved with the input signal.

As the result of the deconvolution, an image signal is acquired in operation S760. The acquired image signal corresponds to a restored image. The restored image is subject to postprocessing, and then displayed via the display unit 220.

Exemplary embodiments have been described above. In the exemplary embodiments, some components which constitute the ultrasonic imaging apparatus 20 may be implemented as modules.

In particular, the term "module" represents a software element or a hardware element, such as a Field Programmable Gate Array (FPGA) or an Application Specific Integrated Circuit (ASIC), and the module performs a predetermined role. However, the module is not limited to software or hardware. Further, the module may be constructed to exist in an addressable storage module, and/or to operate one or more processors.

For instance, the module may include one or more elements (e.g., software elements, object-oriented software elements, class elements and task elements), processors, functions, properties, procedures, subroutines, segments of a program code, drivers, firmware, a microcode, a circuit, data, a database, data structures, tables, arrays, and variables. Herein, functions which are implemented by components and modules may be implemented by a smaller number of combined larger components and modules, or by a larger number of divided smaller components and modules. In addition, the components and modules may be realized to operate one or more central processing units (CPUs) in a device.

In addition to the above-described exemplary embodiments, the present inventive concept can also be embodied as a medium (for example, a transitory or non-transitory computer-readable medium) which includes computer readable codes/commands which are configured to control at least one component of the above-described exemplary embodiments. The medium may include any type of medium that can store and/or transmit the computer readable code.

The computer readable code may be recorded on the medium or transmitted via the Internet, and examples of the medium include a magnetic storage medium (e.g., ROMs, floppy disks, hard disks, etc.), an optical recording medium (e.g., CD-ROMs or DVDs), and a transmission medium such as carrier waves. Further, the medium may include a non-transitory computer-readable medium. In addition, the medium may be distributed to computer systems over a network, in which computer-readable code may be stored and executed in a distributed manner. Furthermore, the processing component may include a processor and/or a computer processor, and may be distributed and/or included in a device.

Although a few exemplary embodiments have been shown and described, it will be appreciated by those skilled in the art that changes may be made in these exemplary embodiments without departing from the principles and spirit of the present inventive concept, the scope of which is defined in the claims and their equivalents.

What is claimed is:

1. An ultrasonic imaging apparatus comprising:
   a probe configured to irradiate ultrasonic waves toward a target area of an object, to receive at least one ultrasonic echo which is reflected from the target area, to convert a received at least one ultrasonic echo into an electrical signal, and to output the electrical signal as an ultrasonic signal;
   a receive beamformer configured to beamform the ultrasonic signal and to output a beamformed ultrasonic signal;
   a point spread function database configured to store a point spread function which is acquired based on a situational variable, and a phase parameter which is determined based on the situational variable, for the beamformed ultrasonic signal; and
   an image generator configured to select an acquired point spread function and a determined phase parameter from the point spread function database based on the beamformed ultrasonic signal, and to perform a deconvolution using an estimated point spread function based on a selected point spread function and a selected phase parameter in order to generate an image,
   wherein the situational variable includes at least one from among a type of the probe, a depth of the target area, and a sound velocity of the ultrasonic waves, and
   wherein the point spread function is acquired based at least in part on the type of the probe.

2. The ultrasonic imaging apparatus according to claim 1, wherein the phase parameter is determined based on a result of a comparison between a shape of a point spread function which is estimated based on information which relates to a magnitude of the beamformed ultrasonic signal and a shape of the acquired point spread function.

3. The ultrasonic imaging apparatus according to claim 1, wherein the point spread function stored in the point spread function database is acquired based on the type of the probe, the depth of the target area, and the sound velocity of the ultrasonic waves.

4. The ultrasonic imaging apparatus according to claim 1, wherein the phase parameter stored in the point spread function database is determined based on the type of the probe and the depth of the target area.

5. The ultrasonic imaging apparatus according to claim 1, wherein the point spread function database stores a two-dimensional (2D) point spread function which is acquired based on the situational variable.

6. The ultrasonic imaging apparatus according to claim 5, wherein the image generator comprises:
   a point spread function selector configured to select a 2D point spread function and a phase parameter from the point spread function database based on a situational variable which relates to the beamformed ultrasonic signal;
   a point spread function estimator configured to estimate a 2D point spread function based on a selected 2D point spread function and the selected phase parameter; and
   a deconvolution unit configured to perform a deconvolution on the beamformed ultrasonic signal using an estimated 2D point spread function.

7. A control method which is executable by an ultrasonic imaging apparatus, comprising:
   generating a point spread function database which stores a point spread function which is acquired based on a situational variable and a phase parameter which is determined based on the situational variable;
   irradiating ultrasonic waves toward a target area of an object, receiving at least one ultrasonic echo which is reflected from the target area, converting a received at least one ultrasonic echo into an electrical signal, and outputting the electrical signal as an ultrasonic signal;

beamforming the ultrasonic signal, and outputting a beamformed ultrasonic signal; and selecting an acquired point spread function and a determined phase parameter from the point spread function database based on the beamformed ultrasonic signal, and performing a deconvolution using a point spread function which is estimated based on a selected point spread function and a selected phase parameter in order to generate an image, wherein the situational variable includes at least one from among a type of a probe which is included in the ultrasonic imaging apparatus, a depth of the target area, and a sound velocity of the ultrasonic waves, and wherein the point spread function is acquired based at least in part on the type of the probe.

8. The control method according to claim 7, wherein the phase parameter is determined based on a result of a comparison between a shape of a point spread function which is estimated based on information which relates to a magnitude of the beamformed ultrasonic signal and a shape of the acquired point spread function.

9. The control method according to claim 7, wherein the point spread function stored in the point spread function database is acquired based on the type of the probe, the depth of the target area, and the sound velocity of the ultrasonic waves.

10. The control method according to claim 7, wherein the phase parameter stored in the point spread function database is determined based on the type of the probe and the depth of the target area.

11. The control method according to claim 7, wherein the point spread function database stores a two-dimensional (2D) point spread function which is acquired based on the situational variable.

12. The control method according to claim 11, wherein the generating the image comprises:

selecting a two-dimensional (2D) point spread function and a phase parameter from the point spread function database based on a situational variable which relates to the beamformed ultrasonic signal;

estimating a 2D point spread function based on a selected 2D point spread function and the selected phase parameter; and performing a deconvolution on the beamformed ultrasonic signal using an estimated 2D point spread function.

13. A non-transitory computer readable recording medium having recorded thereon a program executable by a computer for performing a control method relating to an ultrasonic image, the method comprising:

generating a point spread function database which stores a point spread function which is acquired based on a situational variable and a phase parameter which is determined based on the situational variable;

selecting an acquired point spread function and a determined phase parameter from the point spread function database based on a beamformed ultrasonic signal; and performing a deconvolution using a point spread function which is estimated based on a selected point spread function and a selected phase parameter in order to generate an image, wherein the beamformed ultrasonic signal is generated by an ultrasonic imaging apparatus which is configured to irradiate ultrasonic waves toward a target area of an object, receive at least one ultrasonic echo which is reflected from the target area, convert a received at least one ultrasonic echo into an electrical signal, output the electrical signal as an ultrasonic signal, and beamform the ultrasonic signal, and wherein the situational variable includes at least one from among a type of a probe used by the ultrasonic imaging apparatus, a depth of the target area, and a sound velocity of the ultrasonic waves, and wherein the point spread function is acquired based at least in part on the type of the probe.

14. The non-transitory computer readable medium according to claim 13, wherein the phase parameter is determined based on a result of a comparison between a shape of a point spread function which is estimated based on information which relates to a magnitude of the beamformed ultrasonic signal and a shape of the acquired point spread function.

15. An ultrasonic imaging apparatus comprising:

a probe configured to irradiate ultrasonic waves toward a target area of an object, to receive at least one ultrasonic echo which is reflected from the target area, to convert a received at least one ultrasonic echo into an electrical signal, and to output the electrical signal as an ultrasonic signal; and an image processor configured to perform a deconvolution using an estimated point spread function with respect to an outputted ultrasonic signal in order to generate an image, wherein the estimated point spread function is obtained by using at least one measured two-dimensional point spread function with respect to at least one situational variable which relates to the ultrasonic signal, and wherein the at least one situational variable includes at least one from among a type of the probe, a depth of the target area, and a sound velocity of the ultrasonic waves, and wherein the point spread function is obtained based at least in part on the type of the probe.

16. The ultrasonic imaging apparatus of claim 15, wherein the estimated point spread function is obtained by using the at least one measured two-dimensional point spread function in conjunction with a phase parameter which is determined based on the at least one situational variable.

17. The ultrasonic imaging apparatus of claim 16, wherein the phase parameter is determined based on magnitude information which relates to the ultrasonic signal and a shape of the at least one measured two-dimensional point spread function.

18. The ultrasonic imaging apparatus of claim 16, wherein the image processor is further configured to select the at least one measured two-dimensional point spread function from among a plurality of measured two-dimensional point spread functions based on the at least one situational variable, and to select the phase parameter from among a plurality of phase parameters based on the at least one situational variable.

19. The ultrasonic imaging apparatus of claim 15, further comprising a receive beamformer configured to perform beamforming upon the ultrasonic signal, wherein the image processor is further configured to perform the deconvolution using the estimated point spread function with respect to a beamformed ultrasonic signal in order to generate the image.

20. The ultrasonic imaging apparatus of claim 15, further comprising a transmit beamformer configured to transmit time-delayed signals to the probe, wherein the probe is further configured to use the time-delayed signals to determine a focal point toward which the ultrasonic waves are irradiated.

21. A method for using an ultrasonic imaging apparatus to generate an image, comprising:
- irradiating, by a probe of the ultrasonic imaging apparatus, ultrasonic waves toward a target area of an object;
- receiving, by the probe, at least one ultrasonic echo which is reflected from the target area;
- converting, by the probe, a received at least one ultrasonic echo into an electrical signal;
- outputting, by the probe, the electrical signal as an ultrasonic signal;
- estimating, by an image processor, a point spread function with respect to an outputted ultrasonic signal; and
- performing, by the image processor, a deconvolution using an estimated point spread function with respect to the outputted ultrasonic signal in order to generate the image,
- wherein the estimating the point spread function comprises using at least one measured two-dimensional point spread function with respect to at least one situational variable which relates to the ultrasonic signal,
- wherein the at least one situational variable includes at least one from among a type of the probe, a depth of the target area, and a sound velocity of the ultrasonic waves, and
- wherein the at least one measured two-dimensional point spread function is measured based at least in part on the type of the probe.

22. The method of claim 21, wherein the estimating the point spread function further comprises:
- determining a phase parameter based on the at least one situational variable; and
- using the at least one measured two-dimensional point spread function in conjunction with a determined phase parameter.

23. The method of claim 22, wherein the determining the phase parameter comprises using magnitude information which relates to the ultrasonic signal and a shape of the at least one measured two-dimensional point spread function.

24. The method of claim 22, wherein the estimating the point spread function further comprises selecting the at least one measured two-dimensional point spread function from among a plurality of measured two-dimensional point spread functions based on the at least one situational variable, and the determining the phase parameter comprises selecting the phase parameter from among a plurality of phase parameters based on the at least one situational variable.

25. The method of claim 21, further comprising performing, by a receive beamformer, beamforming upon the ultrasonic signal, wherein the performing the deconvolution comprises using the estimated point spread function with respect to a beamformed ultrasonic signal in order to generate the image.

26. The method of claim 21, further comprising transmitting, by a transmit beamformer, time-delayed signals to the probe, wherein the irradiating the ultrasonic waves comprises using the time-delayed signals to determine a focal point toward which the ultrasonic waves are irradiated.

* * * * *